US006265387B1

(12) United States Patent
Wolff et al.

(10) Patent No.: US 6,265,387 B1
(45) Date of Patent: *Jul. 24, 2001

(54) PROCESS OF DELIVERING NAKED DNA INTO A HEPATOCYTE VIA BILE DUCT

(75) Inventors: Jon A. Wolff; Vladimir Budker, both of Madison; Stuart J. Knechtle, Oregon, all of WI (US)

(73) Assignee: Mirus, Inc.

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 3 days.

(21) Appl. No.: 08/975,573

(22) Filed: Nov. 21, 1997

Related U.S. Application Data

(63) Continuation of application No. 08/571,536, filed on Dec. 13, 1995, now abandoned
(60) Provisional application No. 60/005,091, filed on Oct. 11, 1995.

(51) Int. Cl.$^7$ .......................... A61K 35/00; C12N 15/09; C12N 15/85; C12N 15/00

(52) U.S. Cl. .......................... 514/44; 435/69.1; 435/455; 435/325

(58) Field of Search .............................. 514/44; 435/69.1, 435/455, 325

(56) References Cited

U.S. PATENT DOCUMENTS

| 5,698,531 | * | 12/1997 | Nabel et al. | 514/44 |
| 5,863,904 | * | 1/1999 | Nabel et al. | 514/44 |
| 5,910,488 | * | 4/1999 | Nabel et al. | 514/44 |

OTHER PUBLICATIONS

Chang et al. Science, vol. 267, pp. 518–522, Jan. 1995.*
Steg et al. Circulation, vol. 90, pp. 1648–1656, 1994.*
Barron, L.G. et al., "Cationic Lipids Are Essential For Gene Delivery Mediated By Intravenous Administration Of Lipoplexes." *Gene Therapy* 1999; 6, 1179–1183.
Feldman, L. et al., "Low–Efficiencyof Percutaneous Adenovirus–Mediated Arterial Gene Transfer In The Atherosclerotic Rabbit," *J. Clinical Investigation* 1995; 95:2622–2671.
Lew, D. et al., "Cancer Gene Therapy Using Plasmid DNA: Pharmacokinetic Study of DNA Following Injection in Mice," *Human Gene Therapy* 1995; 6:553–564.
Newman, K. et al., "Adenovirus–Mediated Gene Transfer Into Normal Rabbit Arteries Results In Prolonged Vascular Cell Activation, Inflammation, And Neointimal Hyperplasia," *J. Clinical Investigation* 1995; 96:2955–2965.
Stephan, D. et al., "A New Cationic Liposome DNA Complex Enhances The Efficiency Of Arterial Gene Transfer In Vivo," *Human Gene Therapy* 1996; 7:1803–1812.

Barron, L.G. et al., "Cationic Lipids Are Essential For Gene Delivery Mediated By Intravenous Administration Of Lipoplexes." *Gene Therapy* 1999; 6, 1179–1183.
Acsadi, G. et al., "Direct Gene Transfer and Expression into Rat Heart in Vivo" *The New Biologist*; vol. 3, No. 1 (January Intitative Evaluation of Liver–Specific R991) pp. 71–81.
Barr, E. et al., "Efficient Catheter–mediated Gene Transfer into the Heart using Replication–defective Adenovirus." *Gene Therapy* 1994; 1; 51–58.
Bowling, W.M., et al., "Portal Branch Occlusion Safely Facilitates In Vivo Retroviral Vector Transduction of Rat Liver"*Human Gene Therapy* 7; pp. 2113–2121 (Nov. 10, 1996).
Branchereau, S., et al., "Factors Influencing Retroviral–Mediated Gene Transfer into Hepatocytes In Vivo" *Human Gene Therapy* 5; pp. 803–808, (1994).
Gal, D. et al., "Direct Myocardial Transfection In Two Animal Models: Evaluation of Parameters Affecting Gene Expression and Percutaneous Gene Delivery." *Laboratory Investigation*; vol. 68, No. 1, p. 18, 1993.
Gilgenkrantz, H., et al., "Transient Expression of Genes Transferred In Vivo into Heart Using First–Generation Adenoviral Vectors: Role of the Immune Response." *Human Gene Therapy* 6; pp. 1265–1274 (Oct. 1995).
Hafenrichter, D.G. et al., "Liver–Directed Gene Therapy: Evaluation of Liver Specific Promoter Elements" *Journal of Surgical Research* 56; 510–517 (1994).
Hafenrichter, D.G. et al., "Optimization of Liver–Directed Retroviral Gene Delivery." *Transplantation Proceedings*; vol. 26, No. 6 (Dec.), 1994; pp. 3379–3780.
Hafenrichter, D.G. et al., "Quantitative Promoters From Retroviral Vectors After In Vivo Transduction of Hepatocytes" *Blood*; vol. 84, No. 10 (Nov. 15), 1994: pp. 3394–3404.
Kolodka, T.M. et al., "Hepatic Gene Therapy: Efficient Retroviral–Mediated Gene Transfer into Rat Hepatocytes In Vivo" *Somatic Cell and Molecular Genetics*; vol. 19, No. 5, 1993, pp. 491–497.
Lemarchand, P. et al., "In vivo adenovirus–mediated gene transfer to lungs via pulmonary artery" *Adenovirus Gene Therapy via the Pulmonary Circulation*; pp. 2840–2845.ne Response.
Lin, H. et al., "Expression of Recombinant Genes in Myocardium In Vivo After Direct Injection of DNA" *Circulation*; vol. 82, No. 6, Dec. 1990, pp. 2217–2220.
Lu, X. et al., "Antisense DNA Delivery In Vivo: Liver Targeting by Receptor–Mediated Uptake" *The Journal of Nuclear Medicine*; vol. 35, No. 2, Feb. 1994, pp. 269–275.

(List continued on next page.)

Primary Examiner—Deborah J. R. Clark
Assistant Examiner—Michael C. Wilson
(74) Attorney, Agent, or Firm—Mark K. Johnson

(57) ABSTRACT

A process for delivering a polynucleotide to a parenchymal cell in a mammal by injecting the polynucleotide into a blood vessel connected to the parenchymal cell in tissue or organ of the mammal such that the polynucleotide is transfected into the parenchymal cell and functionally expressed to therapeutic levels.

1 Claim, No Drawings

OTHER PUBLICATIONS

Muhlhauser, J., et al., "In Vivo Angiogenesis Induced by Recombinant Adenovirus Vectors Coding Either for Secreted of Nonsecreted Forms of Acidic Fibroblast Growth Factor" *Human Gene Therapy* 6; pp. 1457–1465 (Nov. 1995).

Nabel, E.G., et al., "Safety and Toxicity of Catheter Gene Delivery to the Pulmonary Vasculature in a Patient with Metastatic Melanoma" *Human Gene Therapy* 5; pp. 1089–1094, (1994).

Ponder, K.P., et al., "Evaluation of Relative Promoter Strength in Primary Hepatocytes Using Optimized Lipofection" *Human Gene Therapy* 2; pp. 41–52 (1991).

Rettinger, S.D. et al., "In Vivo Hepatocyte Transduction with Retrovirus during In–flow Occlusion" *Journal of Surgical Research 54*; 418–425 (1993).

Rettinger, S.D. et al., "Liver–directed gene therapy: Quantitative evaluation of promoter elements by using in vivo retroviral transduction." *Proc. Natl. Acad. Sci. USA*; vol. 91, pp. 1460–1464, Feb. 1994.

Schachtner, S.K et al., "In Vivo Adenovirus–Mediated Gene Transfer Via the Pulmonary Artery of Rats" *Circulation Research*; vol. 76, No. 5, May 1995, pp. 701–709.

Shi, Y. et al., "Transgene Expression in the Coronary Circulation: Transcatheter Gene Delivery." *Gene Therapy* 1994; 1; 404–414.

Soriano P. et al., "Targeted and nontargeted liposomes for in vivo transfer to rat liver cells of a plasmid containing the preproinsulin I gene." *Proc. Matl. Acad. Sci. USA*; vol. 80, pp. 7128–7131, Dec. 1983.

von Harsdorf, R. et al., "Gene Infection Into Canine Myocardium as a Useful Model for Studying Gene Expression in the Heart of Large Mammals" *Gene Expression in the Heart*; pp. 88–695.

* cited by examiner

PROCESS OF DELIVERING NAKED DNA INTO A HEPATOCYTE VIA BILE DUCT

This application is a continuation of Ser. No. 08/571,536, filed Dec. 13, 1995, now abandoned. This application also claims benefit of U.S. Provisional Application No. 60/005,091 filed on Oct. 11, 1995.

FIELD OF THE INVENTION

The invention generally relates to techniques for transferring genes into mammalian parenchymal cells in vivo. More particularly, a method is provided for transfecting parenchymal cells with polynucleotides delivered intravascularly.

BACKGROUND OF THE INVENTION

It was first observed that the in vivo injection of plasmid DNA into muscle enabled the expression of foreign genes in the muscle (Wolff, J A, Malone, R W, Williams, P, et al. Direct gene transfer into mouse muscle in vivo. *Science* 1990;247:1465–1468.). Since that report, several other studies have reported the ability for foreign gene expression following the direct injection of DNA into the parenchyma of other tissues. Naked DNA was expressed following its injection into cardiac muscle (Acsadi, G., Jiao, S., Jani, A., Duke, D., Williams, P., Chong, W., Wolff, J. A. Direct gene transfer and expression into rat heart in vivo. The New Biologist 3(1), 71–81, 1991.), pig epidermis (Hengge, U. R., Chan, E. F., Foster, R. A., Walker, P. S., and Vogel, J. C. Nature Genetics 10: 161–166 (1995)), rabbit thyroid (M. Sikes, B. O'Malley, M. Finegold, and F. Ledley, Hum. Gene Ther. 5, 837 (1994), lung by intratracheal injection (K. B. Meyer, M. M. Thompson, M. Y. Levy, L. G. Barron, F. C. Szoka, Gene Ther. 2, 450 (1995)), into arteries using a hydrogel-coated angioplasty balloon (R. Riessen et al, Human Gene Ther. 4, 749 (1993)) (G. Chapman et al. Circ. Res. 71, 27 (1992)), melanoma tumors (R. G. Vile and I. R art, Cancer Res. 53, 962 (1993)) and rat liver [(Malone, R. W. et al. JBC 269:29903–29907 (1994)) (Hickman, M. A. Human Gene Therapy 5:1477–1483 (1994))].

Another important target tissue for gene therapy is the mammalian liver, given its central role in metabolism and the production of serum proteins. A variety of tecniques have been developed to transfer genes into the liver. Cultured hepatocytes have been genetically modified by retroviral vectors [(Wolff, J. A. et al. PNAS 84:3344–3348 (1987) (Ledley, F. D., Darlington, G. J., Hahn, T. and Woo, S. C. L. PNAS 84:5335–5339 (1987)] and re-implanted back into the livers in animals and in people [(J. R. Chowdhury et al. Science 254, 1802 (1991) (M. Grossman et al. Nature Genetics 6, 335 (1994)]. Retroviral vectors have also been delivered directly to livers in which hepatocyte division was induced by partial hepatectomy [(Kay, M. A. et al Hum Gene Ther. 3:641–647 (1992) (Ferry, N., Duplessis, O., Houssin, D., Danos, O. and Heard, J.-M. PNAS 88:8377–8381 (1991) (Kaleko, M., Garcia, J. V. and Miller, A. D. Hum Gene THer. 2:27–32 (1991)]. The injection of adenoviral vectors into the portal or systemic circulatory systems leads to high levels of foreign gene expression that is transient [(L. D. Stratford-Perricaudet, M. Levrero, J. F. Chasse, M. Perricaudet, P. Briand, Hum. Gene Ther. 1, 241 (1990) (H. A. Jaffe et al. Nat. Genet. 1, 372 (1992) (Q. Li, M. A. Kay, M. Finegold, L. D. Stratford-Perricaudet, S. L. C. Woo, Hum. Gene Ther. 4, 403 (1993)]. Non-viral transfer methods have included polylysine complexes of asialoglycoproteins that are injected into the system circulation [Wu, G. Y. and Wu, C. H. J. Biol. Chem. 263:14621–14624 (1988)].

Foreign gene expression has also been achieved by repetitively injecting naked DNA in isotonic solutions into the liver parenchyma of animals treated with dexamethasone [(Malone, R. W. et al. JBC 269:29903–29907 (1994) (Hickman, M. A. Human Gene Therapy 5:1477–1483 (1994)]. Plasmid DNA expression in the liver has also been achieved via liposomes delivered by tail vein or intraportal routes [(Kaneda, Y., Kunimitsu, I. and Uchida, T. J. Biol. Chem. 264:12126–12129 (1989) (Soriano, P. et al. PNAS 80:7128–7131 (1983) Kaneda, Y., Iwai, K. and Uchida, T. Science 243:375–378 (1989)].

Despite this progress, there is still a need for a gene transfer method that can efficiently and safely cause the expression of foreign genes in the liver in a and/or repetitive manner.

SUMMARY OF THE INVENTION

The present invention provides for the transfer of polynucleotides into parenchymal cells within tissues in situ and in vivo. An intravascular route of administration enables a prepared polynucleotide to be delivered to the parenchymal cells more evenly distributed and more efficiently expressed than direct parenchymal injections. The efficiency of polynucleotide delivery and expression was increased substantially by increasing the permeability of the tissue's blood vessel. This was done by increasing the intravascular hydrostatic (physical) pressure and/or increasing the osmotic pressure. Expression of a foreign DNA was obtained in mammalian liver by intraportally injecting plasmid DNA in a hypertonic solution and transiently clamping the hepatic vein/inferior vena cava. Optimal expression was obtained by clamping the portal vein and injecting the hepatic vein/ inferior vena cava.

A process is described for delivering a polypeptide into a parenchymal cell in a mammal, comprising, transporting the polynucleotide into a vessel communicating with the parenchymal cell of the mammal such that the polynucleotide is transfected into the parenchymal cell.

A process for delivering a coded polynucleotide into a parenchymal cell of a mammal for expression of a protein, comprising, transporting the polynucleotide to a vessel containing a fluid and having a permeable wall; and, increasing the permeability of the wall for a time sufficient to complete delivery of the polynucleotide.

DETAILED DESCRIPTION

A. Definitions

The term, naked polynucleotides, indicates that the polynucleotides are not associated with a transfection reagent or other delivery vehicle that is required for the polynucleotide to be delivered to the parenchymal cell. A transfection reagent is a compound or compounds used in the prior art that bind(s) to or complex(es) with polynucleotides and mediates their entry into cells. The transfection reagent also mediates the binding and internalization of polynucleotides into cells. Examples of transfection reagents include cationic liposomes and lipids, calcium phosphate precipitates, and polylysine complexes. Typically, the transfection reagent has a net positive charge that binds to the polynucleotide's negative charge. The transfection reagent mediates binding of polynucleotides to cell via its positive charge (that binds to the cell membrane's negative charge) or via ligands that bind to receptors in the cell. For example, cationic liposomes or polylysine complexes have net positive charges that enable them to bind to DNA. Other vehicles are also used, in the prior art, to transfer genes into cells. These include complexing the polynucleotides on particles that are then accelerated into the cell. This is termed biolistic or gun techniques. Other methods include eletroporation in which a device is used to give an electric charge to cells. The charge increases the permeability of the cell.

The term polynucleotide is a term of art that refers to a string of at least two base-sugar-phosphate combinations. Nucleotides are the monomeric units of nucleic acid polymers. The term includes deoxyribonucleic acid (DNA) and ribonucleic acid (RNA) in the form of an oligonucleotide messenger RNA, anti-sense, plasmid DNA, parts of a plasmid DNA or genetic material derived from a virus. A polynucleotide is distinguished, here, from a oligonucleotide by containing more than 120 monomeric units. Anti-sense is a polynucleotide that interferes with the function of DNA and/or RNA.

A polynucleotide can be delivered to a cell in order to produce a cellular change that is therapeutic. The delivery of polynucleotides oi other genetic material for therapeutic purposes (the art of improving health in an animal including treatment or prevention of disease) is gene therapy. The polynucleotides are coded to express a whole or partial protein, or may be anti-sense, and can be delivered either directly to the organism in situ or indirectly by transfer to a cell that is then transplanted into the organism. The protein can be missing or defective in an organism as a result of genetic, inherited or acquired defect in its genome. For example, a polynucleotide may be coded to express the protein dystrophin that is missing or defective in Duchenne muscular dystrophy. The coded polynucleotide is delivered to a selected group or groups of cells and incorporated into those cell's genome or remain apart from the cell's genome. Subsequently, dystrophin is produced by the formerly deficient cells. Other examples of imperfect protein production that can be treated with gene therapy include the addition of the protein clotting factors that are missing in the hemophilias and enzymes that are defective in inborn errors of metabolism such as phenylalanine hydroxylase. A delivered polynucleotide can also be therapeutic in acquired disorders such as neurodegenerative disorders, cancer, heart disease, and infections. The polynucleotide has its therapeutic effect by entering the cell. Entry into the cell is required for the polynucleotide to produce the therapeutic protein, to block the production of a protein, or to decrease the amount of a RNA.

Delivery of a polynucleotide means to transfer a polynucleotide from a container outside a mammal to within the outer cell membrane of a cell in the mammal. The term transfection is used herein, in general, as a substitute for the term delivery, or, more specifically, the transfer of a polynucleotide from directly outside a cell membrane to within the cell membrane. If the polynucleotide is a primary RNA transcript that is processed into messenger RNA, a ribosome translates the messenger RNA to produce a protein within the cytoplasm. If the polynucleotide is a DNA, it enters the nucleus where it is transcribed into a messenger RNA that is transported into the cytoplasm where it is translated into a protein. The polynucleotide contains sequences that are required for its transcription and translation. These include promoter and enhancer sequences that are required for initiation. DNA and thus the corresponding messenger RNA (transcribed from the DNA) contains introns that must be spliced, poly A addition sequences, and sequences required for the initiation and termination of its translation into protein. Therefore if a polynucleotide expresses its cognate protein, then it must have entered a cell.

A therapeutic effect of the protein in attenuating or preventing the disease state can be accomplished by the protein either staying within the cell, remaining attached to the cell in the membrane or being secreted and dissociating from the cell where it can enter the general circulation and blood. Secreted proteins that can be therapeutic include hormones, cytokines, growth factors, clotting factors, antiprotease proteins (e.g. alpha-antitrypsin) and other proteins that are present in the blood. Proteins on the membrane can have a therapeutic effect by providing a receptor for the cell to take up a protein or lipoprotein. For example, the low density lipoprotein (LDL) receptor could be expressed in hepatocytes and lower blood cholesterol levels and thereby prevent atherosclerotic lesions that can cause strokes or myocardial infarction. Therapeutic proteins that stay within the cell can be enzymes that clear a circulating toxic metabolite as in phenylketonuria. They can also cause a cancer cell to be less proliferative or cancerous (e.g. less metastatic). A protein within a cell could also interfere with the replication of a virus.

The delivered polynucleotide can stay within the cytoplasm or nucleus apart from the endogenous genetic material. Alternatively, the polynucleotide could recombine (become a part of) the endogenous genetic material. For example, DNA can insert into chromosomal DNA by either homologous or non-homologous recombination.

Parenchymal cells are the distinguishing cells of a gland or organ contained in and supported by the connective tissue framework. The parenchymal cells typically perform a function that is unique to the particular organ. The term "parenchymal" often excludes cells that are common to many organs and tissues such as fibroblasts and endothelial cells within the blood vessels.

In a liver organ, the parenchymal cells include hepatocytes, Kupffer cells and the epithelial cells that line the biliary tract and bile ductules. The major constituent of the liver parenchyma are polyhedral hepatocytes (also known as hepatic cells) that presents at least one side to an hepatic sinusoid and apposed sides to a bile canaliculus. Liver cells that are not parenchymal cells include cells within the blood vessels such as the endothelial cells or fibroblast cells.

In striated muscle, the parenchymal cells include myoblasts, satellite cells, myotubules, and myofibers. In cardiac muscle, the parenchymal cells include the myocardium also known as cardiac muscle fibers or cardiac muscle cells and the cells of the impulse connecting system such as those that constitute the sinoatrial node, atrioventricular node, and atrioventricular bundle.

In a pancreas, the parenchymal cells include cells within the acini such as zymogenic cells, centroacinar cells, and basal or basket cells and cells within the islets of Langerhans such as alpha and beta cells.

In spleen, thymus, lymph nodes and bone marrow, the parenchymal cells include reticular cells and blood cells (or precursors to blood cells) such as lymphocytes, monocytes, plasma cells and macrophages.

In the nervous system which includes the central nervous system (the brain and spinal cord) peripheral nerves, and ganglia, the parenchymal cells include neurons, glial cells, microglial cells, oligodendrocytes, Schwann cells, and epithelial cells of the choroid plexus.

In the kidney, parenchymal cells include cells of collecting tubules and the proximal and distal tubular cells. In the prostate, the parenchyma includes epithelial cells.

In glandular tissues and organs, the parenchymal cells include cells that produce hormones. In the parathyroid glands, the parenchymal cells include the principal cells (chief cells) and oxyphilic cells. In the thyroid gland, the parenchymal cells include follicular epithelial cells and parafollicular cells. In the adrenal glands, the parenchymal cells include the epithelial cells within the adrenal cortex and the polyhedral cells within the adrenal medulla.

In the parenchyma of the gastrointestinal tract such as the esophagus, stomach, and intestines, the parenchymal cells include epithelial cells, glandular cells, basal, and goblet cells.

In the parenchyma of lung, the parenchymal cells include the epithelial cells, mucus cells, goblet cells, and alveolar cells.

In fat tissue, the parenchymal cells include adipose cells or adipocytes. In the skin, the parenchymal cells include the epithelial cells of the epidermis, melanocytes, cells of the sweat glands, and cells of the hair root.

In cartilage, the parenchyma includes chondrocytes. In bone, the parenchyma includes osteoblasts, osteocytes, and osteoclasts.

An intravascular route of administration enables a polynucleotide to be delivered to parenchymal cells more evenly distributed and more efficiently expressed than direct parenchymal injections. Intravascular herein means within a hollow tubular structure called a vessel that is connected to a tissue or organ within the body. Within the cavity of the tubular structure, a bodily fluid flows to or from the body part. Examples of bodily fluid include blood, lymphatic fluid, or bile. Examples of vessels include arteries, arterioles, capillaries, venules, sinusoids, veins, lymphatics, and bile ducts. The intravascular route includes delivery through the blood vessels such as an artery or a vein.

Polypeptide refers to a linear series of amino acid residues connected to one another by peptide bonds between the alpha-amino group and carboxy group of contiguous amino acid residues.

Protein refers to a linear series of greater than 50 amino acid residues connected one to another as in a polypeptide.

Afferent blood vessels of organs are defined as vessels which are directed towards the organ or tissue and in which blood flows towards the organ or tissue under normal physiologic conditions. Conversely, the efferent blood vessels of organs are defined as vessels which are directed away from the organ or tissue and in which blood flows away from the organ or tissue under normal physiologic conditions. In the liver, the hepatic vein is an efferent blood vessel since it normally carries blood away from the liver into the inferior vena cava. Also in the liver, the portal vein and hepatic arteries are afferent blood vessels in relation to the liver since they normally carry blood towards the liver.

B. Delivery of Polynucleotides

In a preferred embodiment of the present invention, a naked polynucleotide is delivered into a liver blood vessel at distal or proximal points. A liver blood vessel includes the portal venous system which transports blood from the gastrointestinal tract and other internal organs (e.g. spleen, pancreas and gall bladder) to the liver. Another liver blood vessel is the hepatic vein. The hepatic vein may also be reached via the inferior vena cava or another blood vessel that ultimately connects to the liver. A needle or catheter is used to inject the polynucleotide into the vascular system. The injection can be performed under direct observation following an incision and visualization of the tissues blood vessels. Alternatively, a catheter can be inserted at a distant site and threaded so that it resides in the vascular system that connects with the target tissue. In another embodiment, the injection could be performed by using a needle that traverses the intact skin and enters a vessel that supplies or drains from the target tissue.

In a preferred embodiment, the liver and portal vein of mice (25 g, 6-week old ICR mice) are visualized through a ventral midline incision. Anesthesia was obtained from intramuscular injections of 1000 $\mu$g of ketamine-HCl (Parke-Davis, Morris Plains, N.J.) in 1 ml of normal saline and methoxyflurane (Pitman-Moore, Mudelein, Ill. USA) which was administered by inhalation as needed. Plasmid DNA in 1 ml of various solutions containing heparin to prevent clotting was injected into the portal vein using a needle over approximately 30 sec. At various times after the injection, the animals were sacrificed by cervical dislocation and the livers (average weight of 1.5 g) were divided into six sections composed of two pieces of median lobe, two pieces of left lateral lobe, the right lateral lobe, and the caudal lobe plus a small piece of right lateral lobe. Each of the six sections were placed separately into an homogenizing buffer. The homogenates were centrifuged and the supernatant analyzed for the foreign gene product. If the gene product is secreted then blood is obtained from the retro-orbital venous sinus and the level of the secreted protein is assayed in the blood. For example, the expression of the human growth hormone gene can be detected by measuring the amount of human growth hormone in the mouse serum using a radioimmnune assay (RIA) (HGH-TGES 100T kit from Nichols Institute, San Juan Capistrano, Calif., USA). Alternatively, the foreign gene could produce an enzyme that corrects an abnormality in the disease state. For example, the phenylalanine hydroxylase gene could be used to normalize the elevated phenylalanine blood levels in a genetic mouse model of phenylketonuria.

In the liver, the hepatic vein is an efferent blood vessel since it normally carries blood away from the liver into the inferior vena cave Also in the liver, the portal vein and hepatic arteries are afferent blood vessels in relation to the liver since they normally carry blood towards the liver. In a preferred embodiment, plasmid DNA may be efficiently expressed if delivered by a retrograde route into the efferent vessel of the liver (i.e. the hepatic vein). As demonstrated in the examples that follow, injections were directed into the inferior cava which was clamped in two locations; proximal and distal to the entry of the hepatic vein into the inferior vena cava. Specifically, the downstream inferior vena cava clamp was placed between the diaphragm and the entry point of the hepatic vein. The upstream inferior vena cava clamp was placed just upstream of the entry point of the renal veins. Since the veins of other organs such as the renal veins enter the inferior vena cava at this location, not all of the injection fluid went into the liver. In some of the animals that received retrograde injections in the inferior vena cava, the hepatic artery, mesenteric artery, and portal vein were clamped (occluded).

C. Permeability

The efficiency of the polynucleotide delivery and expression was increased substantially by increasing the permeability of a blood vessel within the target tissue. Permeability is defined here as the propensity for macromolecules such as polynucleotides to move through vessel walls and enter the extravascular space. One measure of permeability is the rate at which macromolecules move through the vessel wall and out of the vessel. Another measure of permeability is the lack of force that resists the movement through the vessel wall and out of the vessel. Vessels contain elements that prevent macromolecules from leaving the intravascular space (internal cavity of the vessel). These elements include endothelial cells and connective material (e.g. collagen). High permeability indicates that there are fewer of these elements that can block the egress of macromolecules and that the spaces between these elements are larger and more numerous. In this context, high permeability enables a high percentage of polynucleotides being delivered to leave the intravascular space; while low permeability indicates that a low percentage of the polynucleotides will leave the intravascular space.

The permeability of a blood vessel can be increased by increasing the intravascular hydrostatic pressure. In a preferred embodiment, the intravascular hydrostatic pressure is increased by rapidly (from 10 seconds to 30 minutes) injecting a polynucleotide in solution into the blood vessel which increases the hydrostatic pressure. In another preferred embodiment, hydrostatic pressure is increased by obstructing the outflow of the injection solution from the tissue for a period of time sufficient to allow delivery of a polynucleotide. Obstructing means to block or impede the outflow of injection fluid, thereby transiently (reversibly) blocking the outflow of the blood. Furthermore, rapid injection may be combined with obstructing the outflow in yet another preferred embodiment. For example, an afferent vessel supplying an organ is rapidly injected and the efferent vessel draining the tissue is ligated transiently. The efferent vessel (also called the venous outflow or tract) draining outflow from the tissue is also partially or totally clamped for a period of time sufficient to allow delivery of a polynucleotide. In the reverse, an efferent is injected and an afferent vessel is occluded.

In another preferred embodiment, the intravascular pressure of a blood vessel is increased by increasing the osmotic pressure within the blood vessel. Typically, hypertonic solutions containing salts such as NaCl, sugars or polyols such as mannitol are used. Hypertonic means that the osmolality of the injection solution is greater than physiologic osmolality. Isotonic means that the osmolality of the injection solution is the same as the physiological osmolality (the tonicity or osmotic pressure of the solution is similar to that of blood). Hypertonic solutions have increased tonicity and osmotic pressure similar to the osmotic pressure of blood and cause cells to shrink.

The permeability of the blood vessel can also be increased by a biologically-active molecule in another preferred embodiment. A biologically-active molecule is a protein or a simple chemical such as histamine that increases the permeability of the vessel by causing a change in function, activity, or shape of cells within the vessel wall such as the endothelial or smooth muscle cells. Typically, biologically-active molecules interact with a specific receptor or enzyme or protein within the vascular cell to change the vessel's permeability. Biologically-active molecules include vascular permeability factor (VPF) which is also known as vascular endothelial growth factor (VEGF). Another type of biologically-active molecule can also increase permeability by changing the extracellular connective material. For example, an enzyme could digest the extracellular material and increase the number and size of the holes of the connective material.

EXAMPLES

The following examples are intended to illustrate, but not limit, the present invention.

Example 1

Intraportal Injections of Plasmid DNA

Methods

After the livers of 25 g, 6-week old mice were exposed through a ventral midline incision, solutions containing pBS.CMVLux plasmid DNA (described below) were manually injected over approximately 30 sec into the portal vein using a 30-gauge, ½-inch needle and 1-ml syringe. In some animals, a 5×1 mm, Kleinert-Kutz microvessel clip (Edward Weck, Inc., Research Triangle Park, N.C.) was applied during the injection at the junction of the hepatic vein and caudal vena cava. Anesthesia was obtained from intramuscular injections of 1000 $\mu$g of ketamine-HCl (Parke-Davis, Morris Plains, N.J.) in 1 ml of normal saline and methoxyflurane (Pitman-Moore, Mudelein, Ill. USA) which was administered by inhalation as needed. was purchased from Sigma. Heparin was purchased from LyphoMed (Chicago, Ill.).

Reporter Genes and Assays

The pBS.CMVLux, plasmid DNA was used to express luciferase from the human immediate early cytomegalovirus (CMV) promoter (I. Danko, et al.,Gene Therapy 1, 114 (1994) incorporated herein by reference). At two days after injection, the livers were assayed for luciferase expression as previously reported (J. A. Wolff, et al., Science 247,1465 (1990)) except modified as below. The animals were sacrificed by cervical dislocation and the livers (average weight of 1.5 g) were divided into six sections composed of two pieces of median lobe, two pieces of left lateral lobe, the right lateral lobe, and the caudal lobe plus a small piece of right lateral lobe. Each of the six sections were placed separately into 200 $\mu$l of lysis buffer (0.1% Triton X-100, 0.1M K-phosphate, 1 mM DTT pH 7.8) that was then homogenized using a homogenizer PRO 200 (PRO Scientific Inc., Monroe Conn.). The homogenates were centrifuged at 4,000 rpm for 10 min. at 4° C. and 20 $\mu$l of the supernatant were analyzed for luciferase activity. Relative light units (RLU) were converted to pg of luciferase using standards from Analytic Luminescence Laboratories (ALL, San Diego, Calif.). Luciferase protein (pg)=5.1×10$^{-5}$×RLU+ 3.683 ($r^2$ =0.992). Total luciferase/liver was calculated by adding all the sections of each liver and multiplying by 23 to account for dilution effects. For each condition, the mean total luciferase/liver and the associated standard deviation are shown.

Results

After the livers of 25 g, 6-week old mice were exposed through a ventral midline incision, 100 $\mu$g of pBS.CMVLux, plasmid DNA in 1 ml of solutions was injected into the portal vein via a 30-gauge, ½-inch needle over approximately 30 sec. Two days after injection, a mean of only 0.4 ng of total luciferase/liver was produced when the DNA was delivered intraportally in an isotonic solution without ligation of the hepatic vein (Table 1). Inclusion of 20% mannitol in the injection solution increased the mean total luciferase/ liver over ten-fold to 4.8 ng (Table 1).

In order to prevent the DNA's rapid transit and to increase the intraportal hydrostatic pressure, the hepatic vein was clamped for two min after injection. Luciferase production increased another three-fold to 14.7 ng (Table 1).

When the DNA was injected in a hypertonic solution containing 0.9% saline, 15% mannitol and 2.5 units/ml of heparin to prevent microvascular thrombosis and with the hepatic vein clamped, luciferase expression increased eight-fold to 120.3 ng/liver (Table 1). These results are also shown in Table 7 (no dexamethasone condition) in Example 3 below for each individual animal. If the mannitol was omitted under these conditions, luciferase expression was ten-fold less (Table 1).

These results indicate that hypertonicity, heparin and hepatic vein closure are required to achieve very high levels of luciferase expression.

TABLE 1

Mean total luciferase in the liver following the intraportal injection (over 30 seconds) of 100 μg pBS.CMVLux in 1 ml of different solutions with no clamp or with the hepatic vein and inferior vena cava clamped for two minutes.

| Condition | Mean Luciferase (total ng/liver) | Standard Error | Number of Livers |
|---|---|---|---|
| no clamp, normal saline solution (NSS) | 0.4 | 0.7 | n = 6 |
| no clamp, 20% mannitol | 4.8 | 8.1 | n = 3 |
| clamp, 20% mannitol | 14.6 | 26.3 | n = 9 |
| clamp, 2.5 units heparin/ml in NSS | 11.8 | 12.5 | n = 4 |
| clamp, 15% mannitol and 2.5 units heparin/ml in NSS | 120.3 | 101.5 | n = 12 |

Luciferase activities in each liver were evenly distributed in six divided sections assayed (Table 2). All six parts of each liver from all three animals had substantial amounts of luciferase. This is in marked contrast to the direct interstitial, intralobar injection of DNA in which the expression is restricted to the site of injection (R. W. Malone et al., J. Biol. Chem 269, 29903 (1994); M. A. Hickman, et al., Hum. Gene Ther. 5, 1477 (1994) incorporated herein by reference).

TABLE 2

The distribution of luciferase expression over the six liver sections in animals injected intraportally (over 30 seconds) with 100 μg of pBS.CMVux in 1 ml of normal saline solution plus 15% mannitol and 2.5 units heparin/ml and with the hepatic vein clamped for 2 minutes.

| | Total luciferase/Liver (ng/Liver/mouse) | | |
|---|---|---|---|
| Liver Section | Mouse #1 | Mouse #2 | Mouse #3 |
| ½ of median lobe | 496.5 | 66.9 | 304.5 |
| other ½ of median lobe | 177.0 | 126.1 | 241.4 |
| ½ of left lateral lobe | 763.8 | 208.7 | 325.2 |
| other ½ of left lateral lobe | 409.4 | 160.4 | 218.9 |
| right lateral lobe | 527.8 | 129.7 | 216.2 |
| caudal lobe + small piece of right lateral lobe | 374.1 | 149.7 | 240.8 |
| Total | 2,748.6 | 841.5 | 1,547.0 |
| Mean | 458.1 | 140.3 | 257.8 |
| Range | 177–763 | 67–209 | 216–325 |
| Standard Deviation | 194.0 | 46.6 | 45.9 |

Conclusions

1. High levels of luciferase expression were obtained from injecting 100 μg of pBS.CMVLux intraportally.
2. The highest levels of luciferase expression were obtained when the animals were injected intraportally over 30 seconds with 100 μg of pBS.CMVLux in 1 ml of normal saline solution plus 15% mannitol and 2.5 units heparin/ml and with the hepatic vein clamped for 2 minutes.
3. These high levels of expression were consistently obtained in dozens of mice.
4. The luciferase expression was evenly distributed throughout the liver.

Example 2

The effects of other factors on expression were explored using the same methods for the intraportal injection of pBS.CMVLux.

Methods

Unless otherwise specified, the intraportal injections and luciferase assays were done as in Example 1.

Results

Compared to the results with 100 μg of pBS.CMVLUX, luciferase expression was not greater with 500 μg of plasmid DNA (Table 3). Luciferase expression was approximately 7-fold less if 20 μg of pBS.CMVLux DNA was injected instead of 100 μg

TABLE 3

Total luciferase expression in each liver of each animal injected intraportally (over 30 sec) with 20 μg, 100 μg, or 500 μg of pBS.CMVLux in 1 ml of normal saline solution plus 15% mannitol and 2.5 units heparin/ml and with the hepatic vein occluded for 2 min.

| | Total luciferase/Liver (ng/Liver/mouse) | |
|---|---|---|
| Mouse Number | 100 μg pBS.CMVLux | 500 μg pBS.CMVLux |
| 1 | 1,023 | 15 |
| 2 | 178 | 82 |
| 3 | 108 | 23 |
| 4 | 140 | 340 |
| Mean | 362 | 115 |
| Standard Deviation | 441 | 153 |

The times for which the hepatic vein was occluded were varied from 2 min to 4 min to 6 min. In Table 4, one can see that the time of occlusion did not have a large effect on expression.

TABLE 4

Effect of time of hepatic vein occlusion on luciferase expression in animals injected intraportally with 100 μg of pBS.CMVLux in 1 ml of normal saline solution plus 15% mannitol and 2.5 units heparin/ml.

| | Total luciferase/Liver (ng/Liver/mouse) | | |
|---|---|---|---|
| Mouse Number | 2 min | 4 min | 6 min |
| 1 | 4.6 | 1.9 | 32.7 |
| 2 | 44.9 | 11.5 | 6.4 |

The times over which the injections were done were varied from 30 seconds to 1 minute and 2 minutes. In Table 5, one can see that injecting the 1 ml of the DNA solution (100 μg pBS.CMVLux) over 30 seconds enabled the highest levels of luciferase expression. Longer times of injection led to lower levels.

TABLE 5

Effect of length of injection (time it took to inject all of the 1 ml) on luciferase expression in animals injected intraportally with 100 μg of pBS.CMVLux in 1 ml of normal saline solution plus 15% mannitol and 2.5 units heparin/ml and with the hepatic vein occluded for 2 min.

| | Total luciferase/Liver (ng/Liver/mouse) | | |
|---|---|---|---|
| Mouse Number | 30 sec | 1 min | 2 min |
| 1 | 2,697 | 188 | 21.6 |
| 2 | 790 | 13.4 | 19.9 |
| 3 | 1,496 | 141.1 | 11.8 |
| Mean | 1,662 | 114 | 18 |
| Standard Deviation | 964 | 91 | 5 |

If the total volume of the injection fluid was 0.5 ml instead of 1.0 ml, luciferase expression decreased 70-fold (Table 6) suggesting that 0.5 ml was not sufficient to fill the intravascular space and distribute the DNA throughout the parenchyma.

TABLE 6

Total luciferase expression in each liver of each animal injected intraportally (over 30 sec) with 100 μg of pBS.CMVLUX in either 0.5 or 1 ml of normal saline solution plus 15% mannitol and 2.5 units heparin/ml and with the hepatic vein occluded for 2 min.

| | Total luciferase/Liver (ng/Liver/mouse) | |
|---|---|---|
| Mouse Number | 0.5 ml | 1 ml |
| 1 | 1.6 | 51.9 |
| 2 | 4.7 | 124.8 |
| 3 | 0.4 | 266.9 |
| Mean | 2.3 | 147.9 |
| Standard Deviation | 2.3 | 109.4 |

Conclusions

1. The optimal conditions are in fact the conditions first described in example 1: the animals were injected intraportally over 30 seconds with 100 μg of pBS.CMV-Lux in 1 ml of normal saline solution plus 15% mannitol and 2.5 units heparin/ml and with the hepatic vein clamped for 2 minutes.
2. Use of 500 μg of pBS.CMVLux did not enable greater levels of expression but expression was approximately 7-fold less if 20 μg of DNA was used.
3. Occluding the hepatic vein for longer than 2 minutes did not increase expression.
4. Injecting the pBS.CMVLux over 30 seconds gave the highest luciferase levels as compared to injection times longer than 30 seconds.
5. Injecting the pBS.CMVLux in 1 ml gave higher luciferase levels than injecting the pBS.CMVLux in 0.5 ml.

Example 3

Methods

The intraportal injections and luciferase assays were performed as in Example 1 except that some animals received daily subcutaneous injections of 1 mg/kg of dexamethasone (Elkins-Sinn, Cherry Hill, N.J.) starting one day prior to surgery. The conditions for the injections were intraportal injections over 30 seconds with 100 μg of pBS.CMVLux in 1 ml of nornal saline solution plus 15% mannitol and 2.5 units heparin/ml and with the hepatic vein clamped for 2 minutes.

Results

Under the conditions described above (i.e., hypertonic solution containing heparin and hepatic vein closure) into animals that had been injected with daily injections of dexamethasone starting the day prior to plasmid injection, luciferase expression was three-fold greater than the expression without dexamethasone (Table 7).

TABLE 7

The effect of dexamethasone injections on luciferase expression after the intraportal injection of pBS.CMVLux.

| | Total luciferase/Liver (ng/Liver/mouse) | |
|---|---|---|
| Mouse Number | NO Dexamethasone | WITH Dexamethasone |
| 1 | 51.9 | 1,181.1 |
| 2 | 124.8 | 364.7 |
| 3 | 266.9 | 82.8 |
| 4 | 73.7 | 120.5 |
| 5 | 52.6 | 1,022.9 |
| 6 | 7.3 | 178.1 |
| 7 | 146.1 | 107.6 |
| 8 | 231.4 | 140.2 |
| 9 | 271.2 | |
| 10 | 8.7 | |
| 11 | 8.3 | |
| 12 | 201.1 | |
| Mean | 120.3 | 399.8 |
| Standard Deviation | 101.4 | 444.1 |

Dexamethasone could have increased the production of luciferase and the expression of other genes by several mechanisms. They include increasing the amount of plasmid DNA that enters the liver cells by modifying the state of the liver cells. It could also help the liver cells withstand the high pressure. However, the most likely mechanism is that dexamethasone directly stimulates the CMV promoter and thereby directly increases expression of luciferase by stimulating transcription of the luciferase messenger RNA.

The use of dexamethasone demonstrates that using a readily available pharmaceutical, the levels of expression can be substantially increased and regulated.

Conclusion

1. Dexamethasone administration increased luciferase expression from intraportally-injected pBS.CMVLux plasmid DNA three-fold.
2. This demonstrates that the expression from the liver can be regulated using a commonly-used pharmaceutical.

Example 4

Methods

The intraportal injections were performed using the previously stated technique of injections over 30 seconds with 100 μg of plasmid DNA in 1 ml of normal saline solution plus 15% mannitol and 2.5 units heparin/ml and with the hepatic vein clamped for 2 minutes. The mice also received daily subcutaneous injections of 1 mg/kg of dexamethasone (Elkins-Sinn, Cherry Hill, N.J.) starting one day prior to surgery.

The plasmids pBS.CMVLacZ and pBS.CMVnLacZ were used to express a cytoplasmic and nuclear β-galactosidase protein, respectively, from the CMV promoter (Picard, D. & Yamamoto, K. EMBO J. 6:3333–3340, 1987; incorporated herein by reference). They were constructed by placing either a 3.5-kg-HindIII/XbaI β-galactosidase sequence from pSDKLacZpa (Danko, I. et al. Gene Therapy 1:114–121, 1994; incorporated herein by reference) or a sequence encoding a nuclear-localizing -galactosidase (Picard, D. & Yamamoto, K. EMBO J. 6:3333–3340, 1987; incorporated herein by reference) into pBlueCMV (Danko, I. et al. Gene Therapy 1: 114–121, 1994; incorporated herein by reference).

Two days after intraportal injection, the livers were perfused with 1% paraformaldehyde and 1.25% glutaraldehyde in phosphate buffered saline (PBS) and then kept in this solution for one day. After the livers were stored in 30% sucrose, they were cryosectioned. The sections were mounted on slides and stained for 1 hour to one day with a PBS solution (pH 7.5) containing 400 μg/ml X-gal (5-bromo-4-chloro-3-indolyl-β-D-galactoside) (Sigma), 5 mM potassium ferricyanide, 5 mM ferrocyanide, and 1 mM $MgCl_2$. After washing, the sections were then counterstained with hematoxylin and eosin. In the livers injected with the nuclear-localizing β-galactosidase vector, the washing step after hematoxylin incubation was omitted to decrease its nuclear staining.

Results

Having defined the optimal conditions, the types and percentages of transfected cells were determined. After injections of a 100 μg of the cytoplasmic (pBS.CMVLacZ) or the nuclear (pBS.CMVnLacZ) β-galactosidase expression vectors into dexamethasone-treated animals, liver cryosections 10- to 30-μm thick were stained for β-galactosidase using X-gal at pH 7.5 to prevent background staining. Intense blue staining was observed in approximately 1% of the liver cells and was evenly distributed throughout the liver. X-gal incubations for only 1 hour resulted in intensely blue cells; suggesting that the transfected cells expressed relatively large amounts of the foreign genes. Control livers injected with 100 μg of pBS.CMVLux did not contain any positively-stained cells. Necrosis was observed in approximately 10% of the sections. However, some livers with high β-galactosidase expression did not contain any sections with necrosis.

The hepatocytes were identified by their characteristic morphology. For example, many of the cells in the livers injected with the nuclear β-galactosidase vector, pBS.CMVnLacZ, had blue staining in two nuclei, which is a trait only of hepatocytes. Although the majority of the positively-stained cells were hepatocytes a few small, non-hepatocyte cells contained blue staining.

Conclusion

1. Approximately 1% of the liver cells were transfected with the β-galactosidase gene throughout the entire liver.
2. Almost all of the transfected liver cells were hepatocytes.

Example 5

Methods

Luciferase expression in the liver was compared to that in cultured HepG2 hepatocytes in 35-mm plates. Transfections were done using 3 μg of pBS.CMVLux/plate and either 3 μg of Lipofectin (Life Technologies, Bethesda, Md.) or 6 μg of LipofectAMINE (Life Technologies, Bethesda, Md.) per manufacturer's instructions. Two days after transfection, 200 ul of lysis buffer was added to the cultures and 20 ul of the supernatant were analyzed for luciferase activity as in Example 1.

Results

The efficiency of luciferase expression using this technique was compared to other methods of gene transfer both in vitro and in vivo. Transfections performed under optimal conditions with pBS.CMVLUX and Lipofectin or LipofectAMINE (Life Technologies Inc.) in HepG2 hepatocytes in culture (n=8) yielded a mean total of 3.7±4.5 ng luciferase135-mm plate and 2.8±2.0 ng luciferase/35-mm plate. Thus the efficiency of transfection (without dexamethasone) in terms of ng of luciferase/μg of pBS.CMVLUX DNA was approximately 1 ng/μg both in vitro and in vivo.

The published procedure of repetitively and directly injecting naked plasmid DNA into a rat liver lobe was reduced proportionately for mouse liver (R. W. Malone et al., J. Biol. Chem 269, 29903 (1994); M. A. Hickman, et al., Hum. Gene Ther. 5, 1477 (1994); incorporated herein by reference). A total of 100 μg of pBS.CMVLUX in a total volume of 200 ul of normal saline was injected within five different sites (40 ul/site) into the left lateral lobe of 30g mice treated with dexamethasone. A mean total of only 0.1 ng/liver (4 livers; 0.001 ng luciferase/μg DNA) was obtained and the luciferase expression was only present in the injected lobe. Approximately 30-fold more luciferase expression was obtained if the direct intralobar injections were done using 1 ml of injection fluid and clamping the hepatic vein. In the previous studies involving the multiple injections of a total of 500 μg of pCMVL into a liver lobe of dexamethasone-treated rats, a mean of 9.87 ng of luciferase/liver (0.02 ng/μg DNA) was expressed (R. W. Malone et aL, *J. Biol Chem* 269, 29903 (1994); M. A. Hickman, et al, *Hum. Gene Ther.* 5, 1477 (1994)).

With regard to muscle, we typically inject 10 μg of pBS.CMVLUX or pBS.RSVLUX ((Danko, I. et al. Gene Therapy 1:114–121, 1994)) in normal saline into 6–8 mouse quadriceps muscle per experiment. In dozens of experiments, mean total luciferase per muscle was 0.4–1 ng (±0.5–1.2) and the efficiency was 0.04–0.1 ng luciferase/μg DNA.

TABLE 8

Comparison of efficiency of gene transfer in terms of luciferase expressed per μg of pBS.CMVLux plasmid DNA used for the method (ng luciferase/μg DNA).

| Method of Gene Transfer | Mean Total Yield Of Luciferase (ng) | Amount of pBS.CMVLux Used (μg) | Efficiency (ng Luciferase/μg DNA) |
|---|---|---|---|
| Intraportal Mouse Liver (above optimal conditions-Table 1) hepatic vein clamped | 120.3 ± 101.5 n = 12 | 100 | 1.2 |
| HepG2 In Vitro with Lipofectin | 3.7 ± 4.5 (n = 8) | 3 | 1.2 |
| HepG2 In Vitro with LipofectAMINE | 2.8 ± 2.0 (n = 8) | 3 | 0.9 |
| Intralobar Mouse Liver (20 ul/site × 5 sites) hepatic vein not clamped | 0.1 ± 0.1 n = 4 | 100 | 0.001 |
| Intralobar Mouse Liver (1 ml/1 site) hepatic vein clamped | 2.8 ± 5.6 n = 4 | 100 | 0.028 |
| Intralobar Rat Liver (5 sites) from published data (Journal of Biologic Chemistry 269:29903, 1994; Human Gene Therapy 5:1477, 1994) | 9.87 | 500 | 0.02 |
| Intramuscular | 0.4–1 ±0.5–1.2 n > 50 | 10 | 0.04–0.1 |

Conclusions

1. The intraportal delivery of naked DNA was more than an order of magnitude more efficient than interstitial delivery into either liver or muscle and more evenly distributed.

Example 6

Methods

The intraportal injections were done using the above optimal injections which are intraportal injections over 30 seconds with 100 μg of pCMVGH in 1 ml of normal saline solution plus 15% mannitol and 2.5 units heparin/ml and with the hepatic vein clamped for 2 minutes. Some animals received daily intramuscular injections of 100 mg/kg of cyclosporine (Sandimmune, Sandoz) or daily subcutaneous injections of 1 mg/kg of dexamethasone (Elkins-Sinn, Cherry Hill, N.J.), or both starting one day prior to surgery.

The previously described pCMVGH plasmid DNA was used to express human growth hormone (hGH) (C. Andree, et al., Proc. Natl. Acad. Sci. U.S.A. 91, 12188 (1994); incorporated herein by reference). Blood obtained from the retro-orbit sinus was analyzed for serum concentration of hGH using the radioimmune assay (RIA), HGH-TGES 100T kit from Nichols Institute (San Juan Capistrano, Calif.).

Results

Human growth hormone (hGH) was used as a marker gene to assess the ability of this gene transfer technique to produce a therapeutic serum protein (Table 9). Two days after the intraportal injection of 100 μg of pCMVGH under the above optimal conditions, the mean hGH serum concentration was 57±22 ng/ml (n=12) with a range of 21–95 ng/ml. Neither dexamethasone nor cyclosporine pretreatment significantly affected these initial hGH levels. In two animals injected with pBS.CMVLUX, background hGH levels were 0.3±0.1 ng/ml for 4 weeks afterwards.

In humans, normal pulsatile levels of GH peak at approximately 20 ng/ml above baseline values of approximately 1 ng/'nl and can attain concentrations of 10–180 ng/ml after growth hormone releasing hormone (GHRH) stimulation (A. Favia, J. D. Veldhuis, M. O. Thorner, M. L. Vance, J. Clin. Endocrinol. Metab. 68, 535 (1989); R. W. Holl, M. L. Hartman, J. D. Veldhuis, W. M. Taylor, M. O. Thorner, J. Clin. Endocrinol. Metab. 72, 854 (1991); W. S. Evans et al., Am. J. Physiol. 252, E549 (1987); F. P. Alford, H. W. G. Baker, H. G. Burger, J. Clin Endocrinol. Metab. 37, 515 (1973); incorporated herein by reference). The half-life of hGH is approximately 20 min in humans and 4.5 min in mice; hence these serum levels could translate into much higher levels for more stable proteins (S. Peeters and H. G. Friesen, Endocrinol.101, 1164 (1977); A. Favia, J. D. Veldhuis, M. O. Thorner, M. L. Vance, J. Clin. Endocrinol. Metab. 68, 535 (1989); incorporated herein by reference). For example, if a protein such as alpha-antitrypsin has a half-life that is ten times longer than human GH, then the circulating blood levels should be at more than ten times higher given the same efficiency of protein production. Another example is that for hemophilia which requires levels of factor VIII or IX in the range of approximately 1 μg of the clotting factor/ml of blood. Given the increased stability of these clotting factors, then the 0.1 μg/ml of hGH that we can achieve after intraportal injection of the respective gene means that we would be able to obtain therapeutic levels of clotting factors to prevent bleeding in patients with hemophilia. In summary, these results demonstrate that the intraportal naked DNA technique could be used to produce therapeutic levels of a circulating blood protein.

Serial measurements of hGH serum levels enabled the stability of expression in individual mice to be assessed (Table 9). In untreated animals, hGH expression was unstable as in previous studies in which the plasmid DNA was delivered to non-hepatectomized livers using polylysine complexes or intralobar injections of naked DNA.

An immune response could kill hepatocytes expressing the human protein. To test the hypothesis that expression was unstable because of an immune response, hGH levels were followed in animals that received cyclosporine with or without dexamethasone administration (Table 9). After an acute drop off, hGH levels remained at 6–11 ng/ml for four weeks in animals that received both dexamethasone and cylcosporine. In animals that received dexamethasone alone or cyclosporine alone, hGH expression was prolonged as compared to the non-treated animals but not to the same extent as the animals that received both agents. The ability for this gene transfer method to enable expression of a foreign gene should increase its utility.

TABLE 9

Mean serum levels (ng/ml of serum) of human growth hormone (hGH) following intraportal administration of pCMVGH under optimal conditions in mice (2 to 3 animals for each timepoint) receiving various treatments. Optimal conditions are defined as the use of 0.9% saline, 15% mannitol, 2.5 units/ml heparin solution that was intraportally injected with the hepatic vein closed.

| DAYS AFFER INJECTION | NONE | CSA alone | DEX alone | CSA + DEX |
|---|---|---|---|---|
| 2 | 69 | 43 | 72 | 51 |
| 4 | 11 | 8 | 14 | 14 |
| 8 | 3 | 6 | 7 | 13 |
| 12 | 0 | 4 | 7 | 15 |
| 15 | 0 | 3 | 5 | 13 |
| 21 | 0 | 1.5 | 2.6 | 9.7 |
| 28 | 0 | 1 | 2.2 | 7.9 |

Conclusions

1. These results demonstrate that the intraportal naked DNA technique could be used to produce therapeutic levels of a circulating blood protein that is currently used to treat humans.
2. The levels of the circulating blood protein (i.e. hGH) remained elevated for at least one month after a single injection.

Example 7

Methods

After the portal veins of 25 g, 6-week old mice were exposed through a ventral midline incision, 100 μg of pBS.CMVLux plasmid DNA in 0. 5 ml or 1 ml of normal saline solution plus 15% mannitol and 2.5 units heparin/ml were manually injected over 30 seconds into the portal vein near the junction of the splenic vein and portal vein. The portal vein had two clamps placed for 2 minutes distal and proximal to the point of injection so as to direct the injection fluid into only the splenic vein and to prevent the injection fluid from going to the liver or intestines. The injections were done using a 30-gauge, ½-inch needle and 1-ml syringe. 5×1 mm, Kleinert-Kutz microvessel clips (Edward Weck, Inc., Research Triangle Park, N.C.) were used. Anesthesia was obtained from intramuscular injections of 1000 μg of ketamine-HCl (Parke-Davis, Morris Plains, N.J.) and methoxyflurane (Pitman-Moore, Mudelein, Ill. USA) which was administered by inhalation as needed and was purchased from Sigma. Heparin was purchased from LyphoMed (Chicago, Ill.).

Two days after injection the spleens and pancreas were removed and placed in 500 ul of lysis buffer and 20 ul were analyzed for luciferase expression as described above.

Results

Substantial amounts of luciferase activity were obtained in the spleen and pancreas of all four mice with both injection fluids of 0.5 ml and 1 ml.

TABLE 10

Luciferase expression after the intravascular-administration of pBS.CMVLux into the splenic vein via the portal vein.

| | Total luciferase/Organ (pg/organ/mouse) | |
|---|---|---|
| Injection Volume | Spleen | Pancreas |
| 0.5 ml | 814.4 | 97.2 |
| 0.5 ml | 237.3 | 88.7 |
| 1 ml | 168.7 | 109.4 |
| 1 ml | 395.0 | 97.7 |
| Mean | 403.9 | 98.3 |
| Standard Deviation | 289.6 | 8.5 |

Conclusions

1. Intravascularly-administered plasmid DNA can express efficiently in spleen and pancreas.

Example 8

Methods

100 μg of pBS.CMVLux in 10 ml of normal saline solution plus 15% mannitol was injected into the femoral artery of adult rats with the femoral vein clamped. One to four days after injection, the quadricep was removed and cut into 10 equal sections. Each sections were placed into 500 ul of lysis buffer and 20 ul were assayed for luciferase activity as described above.

Results

Substantial amounts of luciferase expression were expressed in the quadriceps following the intravascular delivery of plasmid DNA.

TABLE 11

Luciferase expression in the quadricep of a rat after the injection of 100 μg of pBS.CMVLux into the femoral artery and with the femoral vein clamped.

| Rat Number | Total Luciferase (pg/quadriceps) |
|---|---|
| 1 | 157.5 |
| 2 | 108.8 |
| 3 | 139.2 |
| 4 | 111.3 |
| Mean | 129.2 |
| Standard Deviation | 23.4 |

Conclusions

1. Intravascularly-adrinistered plasmid DNA can express efficiently in muscle.

Example 9

The previous examples involved injections into the afferent blood vessels of organs. In the liver, the hepatic vein is an efferent blood vessel since it normally carries blood away from the liver into the inferior vena cava. Also in the liver, the portal vein and hepatic arteries are afferent blood vessels in relation to the liver since they normally carry blood towards the liver.

These set of experiments were designed to determine whether plasmid DNA could be efficiently expressed if delivered by a retrograde route into the efferent vessel of the liver (i.e. the hepatic vein).

Since another luciferase expression vector was used, pCILuc, the results obtained with the hepatic vein injections were directly compared to results using the above technique of injecting the portal vein.

Methods

100 μg of pCILuc in 1 ml of normal saline solution plus 15% mannitol and 2.5 units heparin/ml were injected over 30 seconds into hepatic vein via the inferior vena cava. Since it was difficult to directly inject the hepatic vein in rodents, the injections were directed into the inferior cava which was clamped in two locations; proximal and distal (i.e. downstream and upstream) to the entry of the hepatic vein into the inferior vena cava. Specifically, the downstream inferior vena cava clamp was placed between the diaphragm and the entry point of the hepatic vein. The upstream inferior vena cava clamp was placed just downstream of the entry point of the renal veins. Therefore, the 1 ml of the injection fluid entered the hepatic vein and the liver. Since the veins of other organs such as the renal veins enter the inferior vena cava at this location, not all of the 1 ml of injection fluid goes into the liver.

In some of the animals that received retrograde injections in the inferior vena cava, the hepatic artery, mesenteric artery, and portal vein were clamped (occluded) for approximately five minutes immediately before and then after the injections. Specifically, the order of placing the clamps were as follows: first on hepatic artery, then portal vein, then downstream vena cava, and then upstream vena cava. It took about three minutes to place all these clamps and then the injections were done. The clamps were left in place for an additional two minutes from the time that the last clamp (upstream vena cava clamp) was placed.

The intraportal injections were performed as stated using optimal intraportal injections over 30 seconds with 100 μg of pCILuc in 1 ml of normal saline solution plus 15% mannitol and 2.5 units heparin/ml and with the hepatic vein clamped for 2 minutes.

Some of the mice also received daily subcutaneous injections of 1 mg/kg of dexamethasone (Elkins-Sinn, Cherry Hill, N.J.) starting one day prior to surgery.

The pCILuc plasmid expresses a cytoplasmic luciferase from the CMV promoter. It was constructed by inserting the cytoplasmic luciferase cDNA into the pCI (Promega Corp., Madison, Wis.) CMV expression vector. Specifically, a NheI/EcoRI restriction digestion fragment containing the cytoplasmic luciferase cDNA was obtained from pSPLuc (Promega Corp.) and inserted into pCI plasmid DNA that was digested with NheI and EcoRI, using conventional recombinant DNA techniques (Sambrook, J., Fritsch, E. F., and Maniatis, T. (1989) in Molecular Cloning Cold Spring Harbor Laboratory Press, Cold Spring Harbor, N.Y.).

Two days after the injections, the luciferase activity was measured as above in six liver sections composed of two pieces of median lobe, two pieces of left lateral lobe, the right lateral lobe, and the caudal lobe plus a small piece of right lateral lobe.

Results

A. Inferior Vena Cava/Hepatic Vein Injections with the Portal Vein and Hepatic Artery clamped (*Injections in animal #3 were not optimal since the fluid leaked during the injections.) Injections were done in 6-week old animals that received dexamethasone.

| | Luciferase Activity (ng) | | |
|---|---|---|---|
| Sections | Animal #1 | Animal #2 | Animal #3 |
| 1 | 5,576.7 | 4,326.4 | 1,527.4 |
| 2 | 8,511.4 | 4,604.2 | 1,531.6 |
| 3 | 5,991.3 | 5,566.1 | 2,121.5 |
| 4 | 6,530.4 | 9,349.8 | 1,806.3 |
| 5 | 8,977.2 | 4,260.1 | 484.2 |
| 6 | 9,668.6 | 6,100.2 | 1,139.3 |
| total liver | 45,255.5 | 34,206.9 | 8,610.4 |
| mean | 29,357.6 | | |
| standard deviation | 18,797.7 | | |

B. Inferior Vena Cava/Hepatic Vein Injections with the Portal Vein and Hepatic Artery clamped. Injections were done in 6-week old animals that did not receive dexamethasone.

| | Luciferase Activity (ng) | |
|---|---|---|
| Sections | Animal #1 | Animal #2 |
| 1 | 360.6 | 506.2 |
| 2 | 413.5 | 724.7 |
| 3 | 463.0 | 626.0 |
| 4 | 515.5 | 758.6 |
| 5 | 351.6 | 664.8 |
| 6 | 437.8 | 749.6 |
| total liver | 2,542.0 | 4,029.8 |
| mean | 3,285.9 | |
| standard deviation | 1,052.1 | |

C. Portal Vein Injections with the Hepatic Vein Clamped in 6 month old mice that received dexamethasone.

| | Luciferase Activity (ng) | | |
|---|---|---|---|
| Sections | Animal #1 | Animal #2 | Animal #3 |
| 1 | 287.4 | 417.0 | 129.2 |
| 2 | 633.7 | 808.1 | 220.5 |
| 3 | 689.8 | 1,096.5 | 328.2 |
| 4 | 957.8 | 1,056.9 | 181.6 |
| 5 | 660.7 | 1,487.4 | 178.6 |
| 6 | 812.4 | 1,276.4 | 233.4 |
| total liver | 4,041.8 | 6,142.2 | 1,271.5 |
| mean | 3,818.5 | | |
| standard deviation | 2,443.0 | | |

D. Portal Vein Injections with the Hepatic Vein Clamped in 6 week old mice that amethasone.

| | Luciferase Activity (ng) | | |
|---|---|---|---|
| Sections | Animal #1 | Animal #2 | Animal #3 |
| 1 | 352.9 | 379.1 | 87.0 |
| 2 | 667.5 | 373.9 | 108.2 |
| 3 | 424.8 | 1,277.9 | 178.4 |
| 4 | 496.3 | 1,308.6 | 111.9 |
| 5 | 375.2 | 296.4 | 162.3 |
| 6 | 434.7 | 628.7 | 123.0 |
| total liver | 2,751.4 | 4,264.7 | 770.9 |
| mean | 2,595.7 | | |
| standard deviation | 1,752.1 | | |

E. Summary Table Comparing the Luciferase Expression Obtained Using the Above Conditions.

| Injection Condition @ | Mean Total Luciferase/Liver (µg/liver) | Times Condition D. |
|---|---|---|
| Condition A | 29.4 | 11.3 × |
| Condition B | 3.3 | 1.27 × |
| Condition C | 3.8 | 1.46 × |
| Condition D | 2.6 | 1.00 × |

Condition A = Inferior Vena Cava/Hepatic Vein Injections with the Portal Vein and Hepatic Artery Clamped in 6 week-old animals that received dexamethasone.
Condition B = Inferior Vena Cava/Hepatic Vein Injections with the Portal Vein and Hepatic Artery not Clamped in 6-week old animals that did not receive dexamethasone.
Condition C = Portal Vein Injections with the Hepatic Vein Clamped in 24 week old mice that received dexamethasone.
Condition D = Portal Vein Injections with the Hepatic Vein Clamped in 6 week old mice that received dexamethasone.

Conclusions

1. Retrograde delivery of plasmid DNA into the efferent vessels of the liver via the hepatic vein/inferior vena cava leads to high levels of gene expression.
2. The highest levels were achieved using this retrograde approach if the afferent vessels to the liver (portal vein and hepatic artery) were occluded.
3. The CILuc plasmid enabled much higher levels of luciferase expression than the pBS.CMVLux plasmid (see above examples) using the portal vein approach in both 6-week old and 6-month old mice.
4. Under all conditions, luciferase expression was evenly distributed throughout all six liver sections.

Example 10

Animals that received injections into the inferior vena cava were assayed for luciferase to determine whether retrograde delivery into the efferent vessels (veins) of other organs enable gene expression.

Methods

In the same animals that were injected using condition A above (Inferior Vena Cava/Hepatic Vein Injections with the Portal Vein and Hepatic Artery Clamped in 6 week-old animals that received dexamethasone), the kidneys were removed and assayed for luciferase as described above.

In the same animals that were injected under condition B above (Inferior Vena Cava/Hepatic Vein Injections with the Portal Vein and Hepatic Artery NOT Clamped in 6-week old animals that did not receive dexamethasone), the adrenal gland and diaphragm muscle, abdominal muscles, and back muscles were removed for luciferase analysis.

Results

A. Luciferase Activity in Kidneys in Animals Injected Under Condition A.

| | Total Luciferase Activity/Kidney (pg/kidney) | | |
|---|---|---|---|
| | Animal #1 | Animal #2 | Animal #3* |
| Right Kidney | 10,827.8 | 7,662.3 | 636.3 |
| Left Kidney | 733.1 | 753.8 | 479.7 |

*Injection fluid leaked.

B. Luciferase Activity in Adrenals and Various Muscles Injected Under Condition B.

| | Total Luciferase Activity/Tissue (pg/tissue) | | |
|---|---|---|---|
| | Animal #7 | Animal #8 | Animal #9 |
| right adrenal | not assayed | 82.0 | 49.9 |
| left adrenal | not assayed | 48.4 | 42.2 |
| diaphragm | 41.9 | 67.9 | 117.6 |
| abdomen | 40.4 | 43.9 | 44.0 |
| back | 37.7 | 40.1 | 40.9 |

Conclusions

1. Retrograde delivery of plasmid DNA into the efferent vessels of several different tissues led to substantial levels of foreign gene expression in the tissues.
2. These tissues include the adrenal glands (suprarenal glands), the diaphragm muscle, back muscles and abdominal muscles.
3. Foreign gene expression in the diaphragm would be especially useful for Duchennes muscular dystrophy since humans with this disorder die from respiratory failure due to fibrosis of the diaphragm muscle The foregoing is considered as illustrative only of the principles of the invention. Further, since numerous modifications and changes will readily occur to those skilled in the art, it is not desired to limit the invention to the exact construction and operation shown and described. Therefore, accordingly, all suitable modifications and equivalents fall within the scope of the invention.

What is claimed is:

1. A method for delivering naked plasmid DNA into a hepatocyte of a mammal comprising:

a) injecting a composition into the bile duct of a mammal, said composition consisting of naked plasmid DNA encoding a protein operably linked to a promoter and a pharmacologically acceptable solution; and b) increasing the permeability of said bile duct to allow the composition through the bile duct wall and into the liver of the mammal such that said plasmid DNA is delivered to a hepatocyte of the liver, and said hepatocyte expresses said protein to a detectable level.

* * * * *